United States Patent [19]

Kensey et al.

[11] Patent Number: 4,795,438
[45] Date of Patent: Jan. 3, 1989

[54] METHOD AND APPARATUS FOR FORMING A RESTRICTION IN A VESSEL, DUCT OR LUMEN

[75] Inventors: Kenneth Kensey, Hinsdale, Ill.; John Nash, Downingtown, Pa.

[73] Assignee: Intravascular Surgical Instruments, Inc., Frazer, Pa.

[21] Appl. No.: 50,185

[22] Filed: May 13, 1987

[51] Int. Cl.$^4$ .............................................. A61B 17/00
[52] U.S. Cl. .................................. 604/22; 128/303 R
[58] Field of Search ................... 128/305, 303 R, 311, 128/1 R, 333; 604/22

[56] References Cited

U.S. PATENT DOCUMENTS

| | | | |
|---|---|---|---|
| 4,109,654 | 6/1978 | Bolduc et al. | 128/1 R X |
| 4,136,695 | 1/1979 | Dafoe | 128/1 R X |
| 4,245,623 | 1/1981 | Erb | 128/1 R |

Primary Examiner—Michael H. Thaler
Attorney, Agent, or Firm—Caesar, Rivise, Bernstein, Cohen & Pokotilow, Ltd.

[57] ABSTRACT

A flexible, small diameter catheter for effecting the formation of a restriction in a vessel, duct or lumen in a living being and methods of using the catheter. The catheter contains a working head arranged for high speed movement with respect to a longitudinal axis of the catheter. The high speed movement of the working head causes the tissue of the vessel, duct or lumen to produce a restriction. In one aspect of the invention the restriction formation is expedited by the expulsion of a liquid and/or particles into the tissue wall adjacent the working head. In another aspect of the invention the working head includes abrasive means thereon for abrading or otherwise sclerosing the tissue of the vessel, duct or lumen adjacent the working head. A sclerosing liquid or a tissue swelling liquid or adhesive agent can also be introduced by the catheter into contact with the tissue of the vessel, duct or lumen to expedite the restriction forming process.

26 Claims, 1 Drawing Sheet

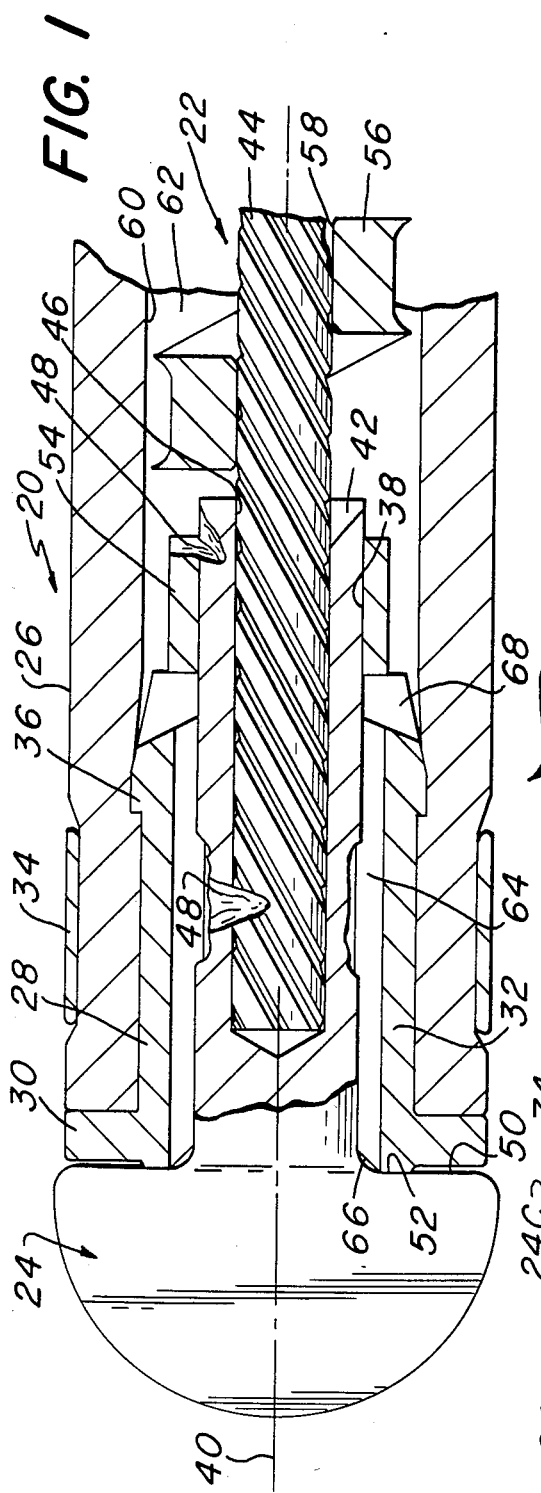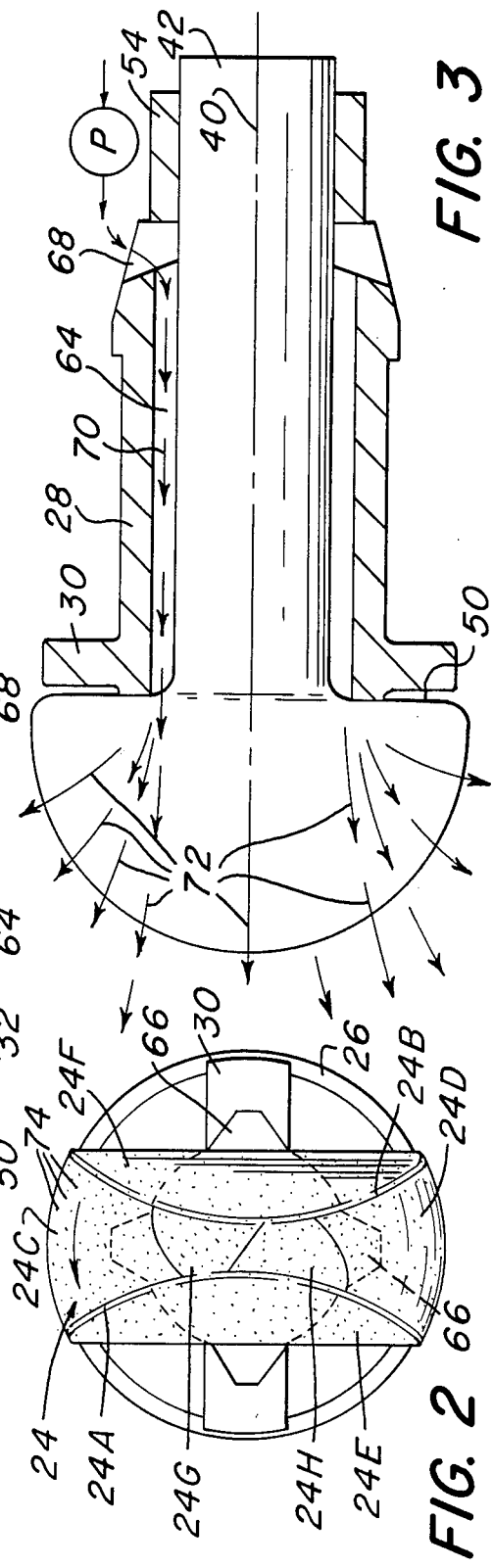

METHOD AND APPARATUS FOR FORMING A RESTRICTION IN A VESSEL, DUCT OR LUMEN

BACKGROUND OF THE INVENTION

This invention relates generally to medical devices and procedures, and more particularly to flexible, power driven catheters for performing surgical and other procedures within a vessel, duct or lumen of a living being.

In U.S. patent application Ser. Nos. 06/765,034, (now U.S. Pat. No. 4,664,112), 06/909,652, (now U.S. Pat. No. 4,681,106), 06/909,802 (now U.S. Pat. No. 4,679,558) and 06/914,954, (now U.S. Pat. No. 4,700,905), filed on Aug. 12, 1985, Sept. 22, 1986, Sept. 22, 1986 and Oct. 3, 1986, respectively, and each entitled Catheter Based Surgical Methods and Apparatus Therefor, of which we are co-inventors, and whose disclosures are incorporated by reference herein there are disclosed and claimed flexible, power driven catheters for performing, with minimum invasion to the body, intravascular surgery and other intralumenar procedures. Among the procedures disclosed and claimed in those applications are the following: peripheral and coronary vascular recanalization via the removal of plaque and/or the dilation of vessels, dilation of small bodily lumens, such as eustachian or fallopian tubes, removal of thrombi, destruction of stones, such as gallstones, kidney stones, bile stones, etc., and in situ valvulectomy.

The catheters disclosed therein basically comprise elongated flexible members having a distal end at which a working head is located. The working head is arranged to be moved at a high rate of speed with respect to the longitudinal axis of the catheter by a drive assembly. In accordance with some preferred aspects of the invention the working head of rotary and is rotated about the longitudinal axis by the drive assembly. The drive assembly includes the elongated drive means for the working head and extending through the catheter from the working head to a first remote, proximal location. The drive assembly includes elongated bearing means which extends down the catheter from a point adjacent the working meas to a second remote, proximal location. One of either the drive means or the bearing means is formed as a spiral of at least one wire wrapped about the other of those means, whereupon the drive means can be rotated freely with respect to the other means and to the catheter to effect the movement, e.g., rotation, of the working head. The drive means and the bearing means cooperate with each other to maintain the drive means at a neutral position within the catheter as the catheter is bent through any arc up to a minimum radiuus of curvature, while enabling the drive means to be rotated at a high rotational speed without resulting in undue vibration which would interfere with the procedure being carried out by the catheter.

Notwithstanding the inventions of our earlier noted applications, the need presently exists for other medical devices or apparatus for performing various other medical and/or surgical procedures or techniques with minimal invasion of the body. In particular, the need presently exists for effecting the formation of a restriction or occlusion in a vessel, duct or lumen of the body, e.g., the formation of a restriction of occlusion of the fallopian tube to sterilize a woman, with minimum invasion of the woman's body.

OBJECTS OF THE INVENTION

Accordingly, it is a general object of this invention to provide an apparatus and methods of use thereof for producing a restriction in a vessel, duct or lumen in a living being.

It is still a further object of the instant invention to provide a catheter having a working head which is arranged for high speed movement to effect a surgical or medical procedure entailing the formation of a restriction in a vessel, duct or lumen in the body of a living being and with minimum invasion to the body.

SUMMARY OF THE INVENTION

These and other objects of the invention are achieved by providing apparatus and a method of using the same. The apparatus is arranged to be introduced into a vessel, duct or lumen in a living being to produce a restriction therein and basically comprises an elongated member having a longitudinal axis and a distal end at which a working head is located. The apparatus is adapted to be inserted longitudinally into the vessel, duct or lumen so that its working head is located adjacent the situs of the restriction to be formed. The apparatus includes drive means to cause the working head to move at a high rate of speed with respect to the axis of the apparatus so that the head movement causes the tissue of the vessel, duct or lumen to produce a restriction.

In accordance with the various aspects of the invention the restriction is formed by the working head effecting the sclerosing of the tissue and/or causing it to swell. The sclerosing action is effected either by the mechanical action, e.g., abrasion, of the working head and/or the expulsion of a sclerosing liquid from the apparatus and into contact with the tissue. The restriction can also be formed by the expulsion of very small particles from the apparatus into contact with the tissue. Moreover, the apparatus may be used to inject an adhesive substance into the vessel, duct or lumen at the site of the restriction to be formed to produce the restriction.

DESCRIPTION OF THE DRAWING

Other objects and many of the attendant advantages of this invention will become readily appreciated when the same becomes better understood by reference to the following detailed description when considered in connection with the accompanying drawing wherein:

FIG. 1 is a side elevational view, partially in section, showing the distal end of a catheter of the subject invention for effecting the methods of the subject invention;

FIG. 2 is a distal end view of the catheter shown in FIG. 1; and

FIG. 3 is a side elevational view of a portion of the distal end of the catheter shown in FIG. 1 and showing the expulsion of fluid and/or particulant material therefrom during the operation of the catheter.

DETAILED DESCRIPTION OF THE PREFERRED EMBODIMENT

Referring now in greater detail to the various figures of the drawing wherein like reference characters refer to like parts, there is shown in FIG. 1 the distal end of a catheter 20 for intravascular or other intralumenar medical or surgical applications, e.g., fallopian tube occlusion.

The catheter 20 is an elongated member including a flexible drive assembly 22 (only a portion of which can be seen in FIG. 1) located therein. The drive assembly is preferably constructed in accordance with the teachings of my co-pending U.S. patent application Ser. Nos. 06/746,220, filed on June 19, 1985, now U.S. Pat. No. 4,686,982 entitled Spiral Wire Bearing For Rotating Wire Drive Catheter, and 06/938,698, filed on Dec. 5, 1986, entitled Catheter With Means to Prevent Wear Debris From Exiting, both applications assigned to the same assignee as this application and whose disclosures are incorporated by reference herein. The drive assemblies disclosed in those applications are particularly suited for in-body surgical and/or medical applications, but can be used for other applications requiring the transmission of power at high speeds and low torque, through a very narrow path, including bends of small, e.g., 0.75 inch (1.9 cm) radiuus of curvature.

Located at the distal end of the catheter 20 is a working head or tool 24. The working head is arranged to be moved at a high speed with respect to the catheter by the drive assembly to effect the procedure to be carried out by the catheter. The proximal end of the drive assembly of the catheter and which is located outside the patient's body is adapted to be connected to a source of rotary power, e.g., an electric motor (not shown). In the preferred embodiment disclosed herein the drive means 22 effects the rotary movement of the working head 24 under the power provided from the remote power source (motor).

In accordance with the preferred embodiment shown herein the working head 24 is arranged to be rotated at a high rate of speed about the longitudinal axis of the catheter. However, if desired, the high speed movement of the working head can be reciprocating longitudinal motion along that axis or the combination of rotary and reciprocating motion with respect to the axis. To that end, the catheter 20 can utilize the teachings of my co-pending U.S. patent application Ser. No. 922,978, filed on Oct. 24, 1986, now U.S. Pat. No. 4,749,376, entitled Reciprocating Working Head Catheter assigned to the same assignee as this invention, and whose disclosure is incorporated by reference herein. In addition, other means for effecting rotary and/or reciprocating motion and/or other types of motion of the working head can be used in the catheter 20.

When the catheter is used for forming a restriction in a vessel, duct or lumen of a living being, such as the fallopian tube, the catheter is introduced os externum and then the catheter is guided into the isthmus of the fallopian tube to the site of the restriction to be formed. This guiding action may be achieved by use of a guiding catheter and/or fiber optic imaging.

The details of the distal end of the embodiment of the catheter 20 shown in FIG. 1 will now be described. As can be seen therein the catheter basically comprises an elongated flexible tubular member or jacket 26 which is formed of a suitable material, e.g., plastic, and which has a small outside diameter. In the preferred embodiment shown herein the outside diameter is approximately 1 mm. (3 French). This size catheter is merely exemplary. Thus, in accordance with this invention, the catheter can be constructed as small as 2 French (0.7 mm.) and as large as 12 French (4 mm.).

At the distal end of the catheter there is secured a sleevelike bushing 28. The bushing includes a flanged end face 30 arranged to abut the end of the catheter's jacket 26 and a tubular portion 32. The outside diameter of portion 32 is approximately that of the inside diameter of the catheter's jacket 26 so that it is snuggly fit therein. The bushing is held firmly in place by a retaining band 34 which tightly encircles the periphery jacket 26 so that plural gripping teeth 36, which are located about the periphery of the tubular portion 28, dig into the interior surface of the catheter jacket 26 and hold the bushing tightly in place therein. The bushing also includes a central bore 38 extending therethrough and aligned with the longitudinal central axis 40 of the catheter. The working head 24 includes a mounting shank or axle 42 projecting proximally and passing through the bore 38 and the bushing 28. A multistrand drive cable 44 constructed in accordance with the teaching of my aforementioned co-pending U.S. patent application Ser. No. 746,220 extends down the catheter's jacket 26 coaxially with axis 40 and terminates and is disposed within a longitudinally extending bore 46 in the shank 42 of the working head 24. The end of the drive cable 44 is secured in place in the bore 46 via a laser weld joint 48.

The construction of the working head 24 will be described later. Suffice if for now to state that the head 24 includes a generally planar rear surface 50 which engages the front surface 52 of the bushing's flange 30. The working head is prevented from axial movement within the bushing 28 by virtue of a retaining ring 54 mounted on the proximal end of the working head axle 42 contiguous with the proximal end of the bushing. The retaining ring is secured to the proximal end of the working head axle via another laser weld 48.

The drive cable 44 is supported in the central position along axis 40 by means of a spiral bearing 56. The spiral bearing is constructed in accordance with the teachings of my aforenoted co-pending U.S. patent application Ser. No. 746,220. Thus, as can be seen the bearing 56 basically comprises a helical or spiral cylindrical coil of wire surrounding the multistrand drive cable 48. The spiral bearing wire 56 extends substantially the entire length of the catheter from a proximally located point adjacent the drive motor (not shown) to the distal end of the catheter. The outer diameter of the bearing coil 56 is sufficiently great so that its loops just clear the interior surface of the catheter's jacket 26 to hold the bearing generally centered on axis 40 in place therein. The inside diameter of the central passageway 58 extending down the length of the bearing coil 56 is just slightly greater than the outside diameter of the drive cable 48 so that the drive cable can freely rotate about axis 40 therein.

It should be pointed out at this junction that the drive cable 44 is preferably drawn or swaged so that its outer periphery has a greater contact surface with the spiral bearing 56 than if the cable were unswaged. This feature is shown and claimed in my aforementioned co-pending U.S. patent application Ser. No. 06/938,698. The inner surface of the spiral wire bearing, that is, the surface forming the passageway 58 extending through the bearing, is substantially linear, e.g., the spiral wire is of generally rectangular cross section, in order to further increase the engaging surface area with the drive cable 44. With a drive assembly constructed as described above, the drive cable 44 can be rotated at a high rate os speed, e.g., from 10,000 to 200,000 rpm, while the catheter is bent through a small radius of curvature, e.g., 0.75 inch (1.9 cm), and without the creation of any standing waves which could result in unwanted vibration to the catheter during its use.

The spacing between the convolutions of the spiral bearing 56, the inner surface 60 of the catheter's jacket 26, and the outer surface drive cable 44 form a passageway 62 through which a material can flow from the proximal end of the catheter to the distal end. That material can be a liquid, e.g., a saline solution, to cool or lubricate the bearing system. Moreover, as will be described in detail later, the catheter is arranged so that the liquid is expelled from the catheter at the working head and into contact with the tissue of the vessel, duct or lumen located adjacent thereto to aid in the restriction forming process. As will also be described in detail later the liquid, or some other fluid, such as a slurry, can be used to carry a stream of very small, micron size, particles, down the catheter and to the working head, whereupon the particles are expelled thereat and into contact with the tissue of the vessel, duct or lumen located adjacent thereto in order to aid in the restriction forming process.

The means for enabling the fluid and/or particles to exit the catheter at its distal end will now be described. Thus, as can be seen in the figures, four, equidistantly spaced grooves, 64 extend down the central bore 46 of the bushing 28. The distal end of each groove 64 terminates at a fluid exit port 66 located at the distal end of flange 30 of the bushing, while the proximal end of each groove 64 terminates in a respective generally radially extending relieved groove 68. The fluid and/or particles carried by the fluid (and not shown due to their very small size) flow down the catheter in the direction of arrows 70 under pressure, denoted by the reference character P in FIG. 3, into the relieved grooves 68, through the associated longitudinal grooves 64 and out through the ports 66 at the end face of the catheter closely adjacent to the longitudinal axis. The shape of the working head 24, as will be described hereinafter, imparts momentum to the liquid and/or particles as it rotates about axis 40, whereupon the liquid and/or particles flow out of the catheter in a generally hemispherical pattern in the directions of arrows 72 as shown in FIG. 3, and which will be described later.

As seen clearly in FIG. 2 the working head 24 basically comprises a convex shaped tip of generally hemispherical shape including a pair of non-sharp impacting surfaces 24A and 24B. The impacting surfaces 24A and 24B are formed by rounded or radiussed edges of a respective pair of cam surfaces 24C and 24D. Those surfaces are formed by the convex outer portions of the working head 24 located between a pair of relieved, e.g., flat surfaces 24E and 24F. Thus, the cam surfaces 24C and 24D are sections of the surface of a sphere. The interface of the cam surfaces 24C and 24D with the relieved surfaces 24E and 24F are substantially rounded (radiussed), e.g., 0.1 mm, so that each interface surface is not sharp (although in the scale of the drawings herein it may appear to be a somewhat sharp line). The relieved surfaces 24E and 24F taper toward each other in a direction toward the distal end of the working head, with the maximum spacing between the relieved surfaces being approximately the diameter of the working head axle or shaft 42. Thus, the flat or relieved surfaces are at a negative rake angle to the cam surfaces.

As can be seen in FIG. 2 the portion of the working head cam surfaces 24C and 24D contiguous with the rotational axis 40 is relieved by the formation of two diametrically opposed planar sections 24G and 24H. The radiussed surfaces at the interface of the cam surfaces and the planar relieved surfaces have approximately a zero degree clearance, while the radiussed surfaces at the interface of the cam surfaces and the relieved surfaces form a ten (10) degree clearance. Thus, the working head 24 has zero clearance at large radial distances from the rotational axis and ten degree clearance at small radial distances. This feature compensates for the lower velocity of the radiussed surfaces at smaller radial distances.

As can be seen clearly in FIG. 2 by virtue of the shape of the working head 24 as described above the fluid exit ports 66 at the distal end of any two diametrically opposed grooves are uncovered or exposed by the relieved surfaces 24E and 24F to enable fluid and/or particles passing through those grooves to exit the ports. As will be appreciated by those skilled in the art, since the working head rotates, the relieved surfaces of the working head sequentially cover and uncover the diametrically opposed ports 66 at the distal end of the grooves. Thus, the fluid and/or particle jets exiting at the distal end of the catheter are immediately accelerated laterally by the relieved, e.g., flatted surfaces. The fluid and/or particle stream is thus broken up into small segments, bullets or slugs, denoted by the arrows 72 and which develop considerable momentum as they are flung radially outward toward the wall of the vessel, duct or lumen. These fluid and/or particle slugs thus impact the tissue contiguous with the working head and transfer their momentum thereto.

In accordance with one method aspect of this invention the fluid comprises a saline solution, or some other liquid, which, when it impacts the tissue adjacent the working head, causes the tissue to swell so that the passageway in the vessel, duct or lumen is restricted, e.g., partially or fully occluded. In accordance with another aspect of this invention, liquid may be a sclerosing liquid, e.g., hypertonic or hypotonic saline, alcohol, etc., so that when it is expelled at the working head and into contact with the vessel, duct or lumen tissue contiguous with the working head that tissue is sclerosed, whereupon it forms a restriction thereat. In accordance with yet another aspect of the method of this invention, the fluid may include a multitude of extremely small, e.g., micron size, particles, which are expelled radially at the working head so they are embedded in the tissue contiguous therewith. These particles may be in the form of an inert material, e.g., Teflon, or may be formed of an active material, so that once embedded they cause the tissue to change, e.g., form scar tissue, whereupon a restriction is created thereat.

In accordance with another aspect of this invention, the restriction in the vessel, duct or lumen may be formed by a mechanical sclerosis and/or abrading action of the moving working head itself. In this connection, the working head may include a plurality of very fine abrasion particles 74, e.g., diamond or boron nitride grit in the range of 5-200 microns, on its outer surfaces. Accordingly, the high speed rotation of the working head causes the abrasive particles to slightly sclerose or abrade the tissue, thereby causing the tissue to form a restriction thereat.

In accordance with another aspect of this invention the catheter may be used to introduce and distribute an adhesive agent into the vessel, duct or lumen at the site of the restriction. This adhesive may be used by itself to effect the formation of the restriction or may work in conjunction with the other process(es) disclosed herein to aid in the restriction forming process.

Without further elaboration the foregoing will so fully illustrate our invention that others may, by applying current or future knowledge, adopt the same for use under various conditions of service.

We claim:

1. The method of producing a restriction at a predetermined location within a vessel, duct or lumen in a living being by utilizing an elongated device having a longitudinal axis and a rotatable working head located adjacent the distal ends of said device, said method comprising the steps of inserting said device into said vessel, duct or lumen so that said working head is at said predetermined location, said working head being arranged for high speed rotary movement with respect to said axis by associated drive means, causing said drive means to rotate said working head at a high speed, and employing rotary energy from said rotating working head to aid in providing a restriction in said vessel, duct or lumen.

2. The method of claim 1 wherein said device comprises an elongated, small diameter, flexible catheter which is introduced into said vessel, duct or lumen, and wherein said method additionally comprises the step of moving said device along said vessel, duct or lumen until its working head is located at said predetermined location.

3. The method of claim 2 wherein said rotation of said working head results in the mechanical sclerosis of tissue of said vessel, duct or lumen to produce said restriction.

4. The method of claim 2 including the step of introducing a restriction forming agent into said vessel, duct or lumen in the region of the rotating working head for cooperating with said rotating working head to expedite the formation of said restriction.

5. The method of claim 4 wherein said rotating working head cooperates with the restriction forming agent by propelling said restriction forming agent generally radially from said catheter into engagement with tissue of said vessel, duct or lumen.

6. The method of claim 1 wherein said rotation of said working head results in the mechanical sclerosis of tissue of said vessel, duct or lumen to produce said restriction.

7. The method of claim 1 including the step of introducing a restriction forming agent into said vessel, duct or lumen in the region of the rotating working head for cooperating with said rotating working head to expedite the formation of said restriction.

8. The method of claim 7 wherein said rotating working head cooperates with the restriction forming agent by propelling said restriction forming agent generally radially from said device into engagement with tissue of said vessel, duct or lumen.

9. The method of claim 7 wherein said restriction forming agent is a liquid which affects the swelling of said tissue to produce said restriction.

10. The method of claim 5 wherein said restriction forming agent is a sclerosing liquid which causes said tissue to produce said restriction.

11. The method of claim 1 additionally comprising the step of introducing a plurality of particles into the region of the rotating working head whereat the rotating working head cooperates with the particles to direct said particles into contact with tissue of said vessel, duct or lumen at said predetermined location to produce said restriction thereat.

12. The method of claim 11 wherein said particles are disposed in a liquid which is expelled from said device by cooperating with said rotating working head.

13. The method of claim 1 additionally comprising the step of introducing an adhesive agent into said vessel, duct or lumen in the region of the rotating working head whereat said rotating working head affects distribution of said adhesive agent into contact with tissue forming said vessel, duct or lumen to expedite the formation of said restriction at said predetermined location.

14. Apparatus for producing a restriction at a predetermined location within a vessel, duct or lumen in a living being, said apparatus comprising a elongated member having a longitudinal axis and a distal end at which a rotatable working head is located, said apparatus being adapted to be inserted longitudinally in said vessel, duct or lumen so that said working head is located adjacent the situs of the restriction to be formed, said apparatus including drive means for causing said working head to rotate with respect to said axis at a high rate of speed for creating rotary energy which is employed to produce a restriction at said predetermined location in said vessel, duct or lumen.

15. The apparatus of claim 14 wherein said working head is constructed to affect the sclerosis of said tissue to produce said restriction.

16. The apparatus of claim 15 wherein said working head includes abrading means to affect the sclerosis of said tissue.

17. The apparatus of claim 16 wherein said abrading means comprises a plurality of very small abrasive particles.

18. The apparatus of claim 14 wherein said apparatus comprises a flexible, small diameter, catheter.

19. The apparatus of claim 18 wherein said working head is constructed to affect the mechanical sclerosis of said tissue to produce said restriction.

20. The apparatus of claim 19 wherein said working head includes abrading means to affect the sclerosis of said tissue.

21. The apparatus of claim 20 wherein said abrading means comprises a plurality of very small abrasive particles.

22. The apparatus of claim 18 additionally comprising means for ejecting a restriction forming agent out of said catheter in the region of the rotating working head whereat said rotating working head cooperates with the restriction forming agent to direct said agent into contact with tissue of said vessel, duct or lumen to expedite the formation of said restriction.

23. The apparatus of claim 22 wherein said means for ejecting a restriction forming agent is a means for ejecting a sclerosing liquid.

24. The apparatus of claim 22 wherein said means for ejecting a restriction forming agent is a means for ejecting a plurality of very small particles.

25. The apparatus of claim 22 wherein said means for ejecting a restriction forming agent is a means for ejecting a liquid which causes said tissue to swell to produce said restriction.

26. The apparatus of claim 22 wherein said rotating working head cooperates with said restriction forming agent for expelling at least a portion of said agent radially from said catheter into contact with the tissue of said vessel, duct or lumen.

* * * * *